United States Patent [19]

Miyamae

[11] Patent Number: 4,741,338

[45] Date of Patent: May 3, 1988

[54] THERMOELECTRIC PHYSICAL REMEDY APPARATUS

[76] Inventor: Toshiaki Miyamae, 9-15, 1-Chome, Nakagawa-nishi, Ikuno-ku, Osaka, Japan

[21] Appl. No.: 915,756

[22] Filed: Oct. 6, 1986

[51] Int. Cl.⁴ .................................................. A61F 7/00
[52] U.S. Cl. ..................................... 128/399; 128/362; 128/384
[58] Field of Search ............... 128/362, 384, 387, 388, 128/389, 399, 379

[56] References Cited

U.S. PATENT DOCUMENTS

| | | | |
|---|---|---|---|
| 1,720,002 | 7/1929 | Reynolds | 128/384 |
| 2,938,356 | 5/1960 | McMahon | 128/384 |
| 3,080,723 | 3/1963 | Price | 128/387 |
| 4,523,594 | 6/1985 | Kuznetz | 128/399 |
| 4,585,002 | 4/1986 | Kissin | 128/399 |

Primary Examiner—Carl D. Friedman
Assistant Examiner—Michael Safavi
Attorney, Agent, or Firm—Moonray Kojima

[57] ABSTRACT

The present invention relates to a thermoelectric physical remedy apparatus applicable to physical remedy processes for dealing with weight-reduction beauty-treatment like removal of superfluous flesh from abdomen for example, contusion, sprain, muscular fatigue, and others, which features compact size of the entire unit, easy application in house holds, and easy switching between high and low temperature by means of covering thermoelectric elements with the externally exposed junction pieces of thermoelectric elements as well as by providing soft external housing unit containing ventilation path.

4 Claims, 2 Drawing Sheets

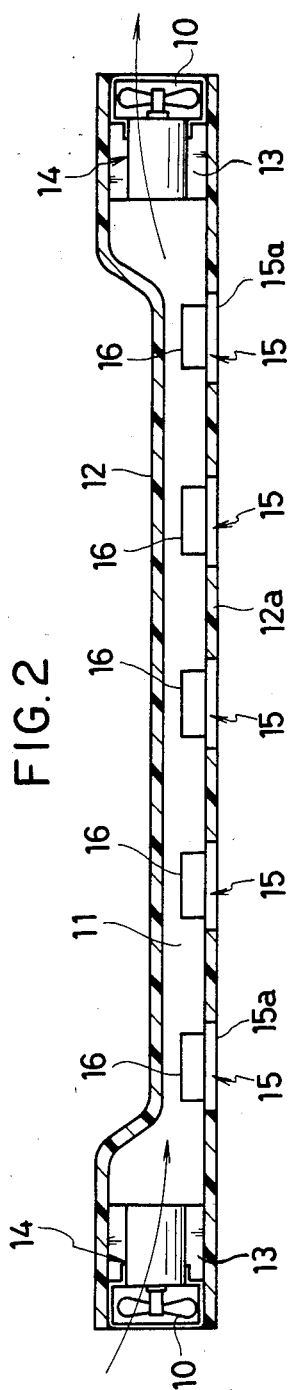
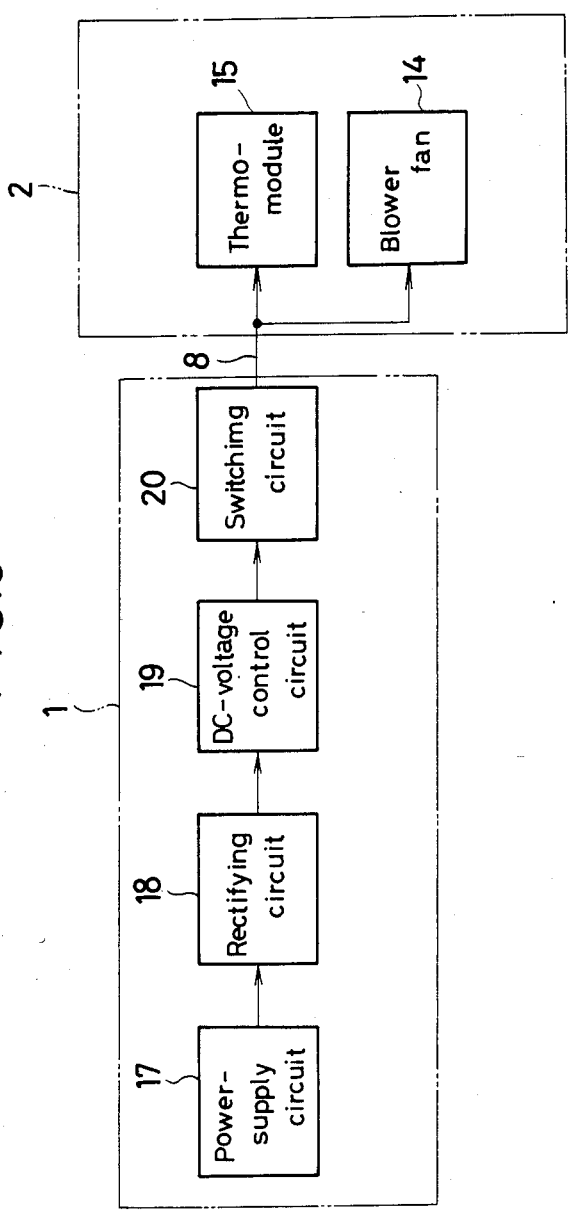
FIG.2
FIG.3

THERMOELECTRIC PHYSICAL REMEDY APPARATUS

BACKGROUND OF THE INVENTION

Conventionally, there are a variety of physical remedy apparatuses including the one that diminishes subcutaneous fat from abdomen for promoting weight-reduction beauty treatment like a device that discharges either pressurized air or water from the tip of nozzle for stimulating abdomen using applied pressure for example, or such a device that diminishes subcutaneous fat from abdomen by promoting blood circulation simultaneous with stimulation by controlling temperature of pressurized air or water to either raise or lower temperature. Nevertheless, these conventional devices still had problems to solve. More particularly, any of these devices needed a large-scale supplementary units such as a compressor for generating a specific pneumatic or hydraulic pressure. Since provision of any supplentary unit unavoidably results in the enlarged configuration of the entire system, it prevents households from easily using any of these.

OBJECT OF THE INVENTION

The primary object of the present invention is to provide a novel thermoelectric physical remedy apparatus which is capable of effectively applying stimulation to abdomen and promoting faster blood circulation and perspiration to eventually diminish or remove superfluous flesh from abdomen by repeating hot and cold temperature cycles by placing junction pieces onto abdomen via cloth by effectively causing junction pieces to be heated and cooled by means of Peltier effect by inversing the polarity of DC power-supply source applied to the thermoelectric elements like thermomodule for example.

Another object of the present invention is to provide a novel thermoelectric physical remedy apparatus which allows any household to easily use it by dispensing with any of large-size supplementary units a compressor otherwise needed for any conventional systems, thus resulting in the significantly compact constitution of the entire unit.

A still another object of the present invention is to provide a novel thermoelectric physical remedy apparatus which is capable of easily switching the junction pieces from the heated condition (i.e., generation of heat) to the cooled condition (i.e., absorption of heat) by merely shifting the direction of DC powder source applied to said thermoelectric electric elements between the positive and negative poles by switching means for example.

A still further object of the present invention is to provide a novel thermoelectric physical remedy apparatus which is capable of promoting the heat absorption and radiation effect by allowing air to pass through a ventilation path formed inside of soft-material external housing covering the thermoelectric elements.

A still further object of the present invention is to provide a novel thermoelectric physical remedy apparatus which is capable of executing multifunctional treatments merely by applying this apparatus using soft-material external housing that can smoothly come into contact with any affected part including hands, legs, and other body parts suffering from either contusion, sprain, or muscular fatigue, in addition to abdomen part for diminishing subcutaneous fat.

Still further objects of the present invention will be better understood from the detailed description given hereinbelow and the accompanying drawings which are provided by way of illustration only, and thus are not limitative of the present invention.

BRIEF DESCRIPTION OF THE DRAWINGS

FIG. 2 is the sectional view of the thermoelectric physical remedy apparatus reflecting one of the preferred embodiments of the present invention; and FIG. 3 is the simplified block diagram denoting the constitution of the circuit of the thermoelectric physical remedy apparatus related to the present invention.

DESCRIPTION OF THE PREFERRED EMBODIMENTS

Figure 1:
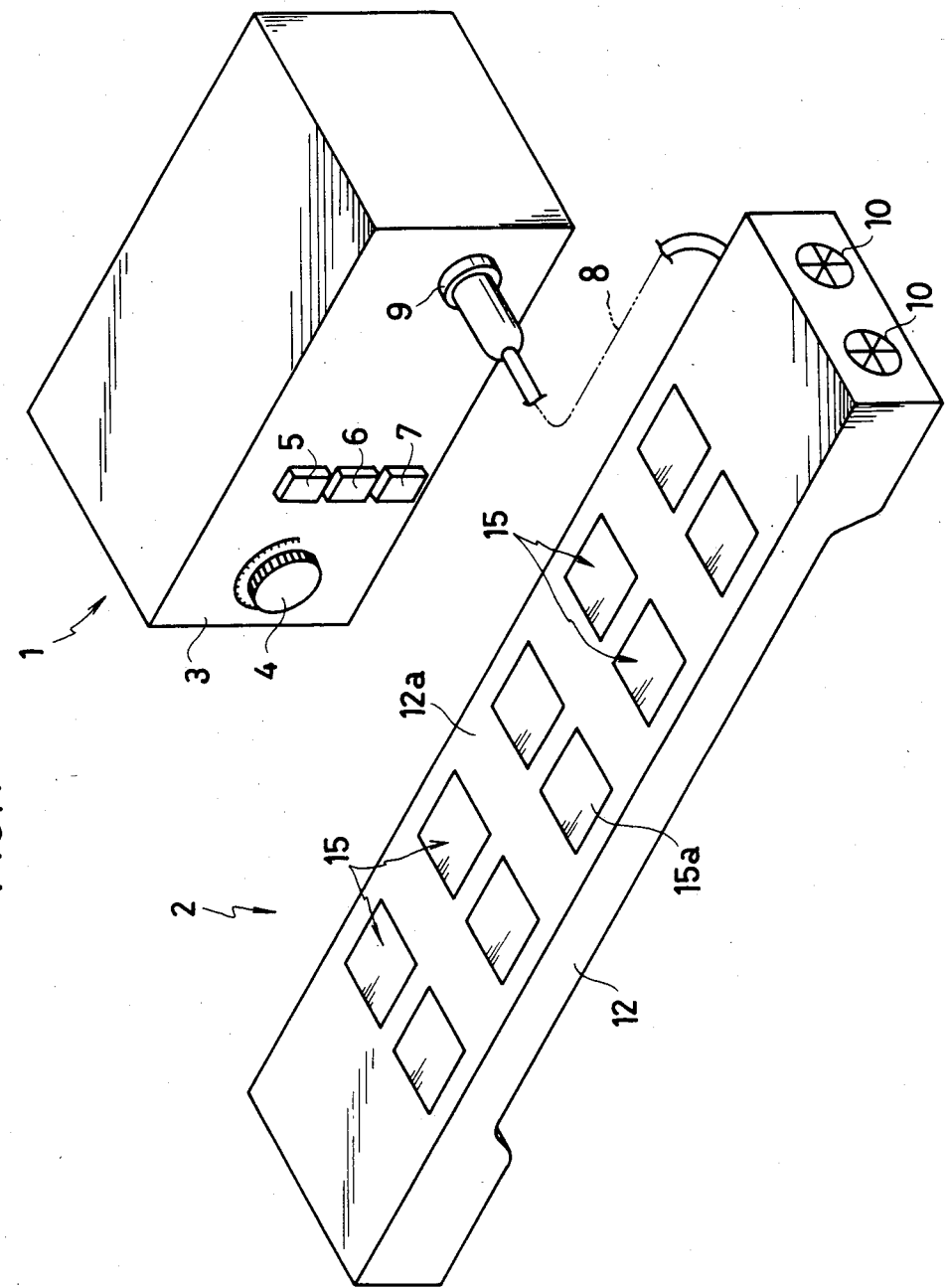
FIG. 1 is the perspective view of the thermoelectric physical remedy apparatus denoting one of the preferred embodiments of the present invention.

Referring more particularly to the accompanying drawings, one of the preferred embodiments of the present invention is described below.

Drawings denote the constitution of the thermoelectric physical remedy apparatus related to the present invention, in which FIG. 1 denotes that the thermoelectric physical remedy apparatus is provided with controller unit 1 and thermoelectric part 2. Housing 3 of the controller unit 1 is provided with temperature-adjusting knob 4, cooling switcii 5, heating switch 6, automatic cold-temperature switch 7, and connector 9 of the connection cable 8.

As shown in FIGS. 1 and 2, the thermoelectric part 2 is provided with the following: Ventilation apertures 10 and 10 in both ends in its length direction, belt-like external cover 12 made from soft polyvinyl chloride internally provided with ventilation path 11, blower fans 14 and 14 provided inside of ventilation apertures 10 and 10 of the belt-like external cover 12 via supporter member 13, and a total of 10 pieces of thermo-modules 15 which are substantially the thermoelectric elements aligned in two rows on the front surface of the belt-like external cover for example.

Each of these thermo-modules (or called thermoelements) 15 contains a plurality of metal pieces or metallic compound pieces being connected to each other in series between upper and lower flat ceramic plates with the lower ceramic plate being shown at 15a. These thermo-modules 15 are respectively held by a flexible belt-like external cover, in which the flat ceramic plates 15a functioning as junction pieces are external bared as shown in FIG. 1. A plurality of heat-radiating fins 16 are provided for the internal surface of each thermo-module 15. Each of these thermo-modules 15 radiates and absorbs heat by applying the incoming DC current in accordance with Peltier effect. Functions of the thermo-module used for the thermoelectric physical remedy apparatus related to the present invention are denoted by the equation show below;

$$Q = \beta I$$

where Q denotes the quantity of heat generated and/or absorbed, I denotes the DC current flowing through these elements, and $\beta$ denotes proportional constant corresponding to Peltier coefficient.

Note that Peltier coefficient $\beta$ is equal to the multiple of Seebeck coefficient $\alpha$ and the absolute temperature, i.e., $\beta = \alpha T$. When the direction of the flowing DC current is inversed, generation of heat is converted into aborption of heat and vice versa.

Normally, each of these thermo-modules 15 is heated to a specific temperature corresponding to the sum of normal temperature and 20° through 25° C. to a maximum of 100° C. during the heating cycle. Conversely, when the cooling cycle is entered, temperature is lowered to a certain level about 15° C. below the normal temperature to a minimum of −20° C.

FIG. 3 is the simplified block diagram of the thermoelectric electric physical remedy apparatus related to the present invention. The commercial power-supply circuit 17 feeding 100 V AC for example is connected to the following full-wave rectifier circuit 18 incorporating diode bridge, smoothing capacitor, and other elements for example in order that the commercial AC power can be rectified and smoothened into the designated DC current by the full-wave rectifier circuit 18.

This circuit 18 is connected to the following DC-voltage control circuit 19 including temperature-adjusting knob 4. The DC-voltage control circuit 19 generates about 7 V DC/2A of the rated DC power source, while it also variably controls DC voltage and current output from the circuit 19 itself by applying voltage-varying volume connected to knob 4.

The output terminal of this DC-voltage is connected to switching circuit 20 containing switches 5 through 7, while the switching circuit 20 is connected to blower fan 14 and each of these thermo-modules 15 via connection cable 8.

When cooling switch 5 of the switching circuit 20 is activated, each of these thermo-modules 15 absorbs heat. When heating switch 6 is activated, each of these thermomodules generates heat, whereas when the automatic cold-hot temperature alternating switch 7 is activated, each of these thermo-modules alternately executes generation and absorption of heat at about 1 minute intervals.

Referring now to the accompanying drawings, functions of the thermoelectric physical remedy apparatus related to the present invention are described below.

For example, to diminished superfluous flesh from abdomen part of a man, belt-like external cover securing a plurality of thermo-modules and being made from soft PVC material is first placed onto the abdomen part via underwears. Next, he turns the power switch (not shown) ON and rotates the temperature-adjusting knob 4 to a desired position, and then when he turns the automatic hot-cold temperature alternating switch ON, each of these thermo-modules alternately repeats heating and cooling cycles at about 1 minute intervals.

By repeatedly and alternately applying hot and cold temperature at specific intervals, stimulation is repeatedly applied to the abdomen part, while simultaneously promoting faster blood circulation and perspiration as well, and a result, superfluous flesh can eventually be eliminated from the abdomen part.

In particular, since the thermoelectric physical remedy apparatus embodied by the present invention dispenses with a large-dimensional compressor otherwise needed for any conventional apparatus of this kind, the entire apparatus related to the present invention can be built in a compact size, thus allowing anyone to easily operate it at home.

In addition, unlike a conventional hot-temperatureapplied moxa cautery, by turning the DC current delivered to each of these thermo-modules 15 over to either of switches 5 and 6 or to the automatic hot-cold temperature alternating switch 7 of switching circuit 20, the junction piece 15a can easily be switched from the heated condition (generation of heat) into the cooling condition (absorption of heat). This is extremely effective for applying remedy like elimination of subcutaneous fat for example.

Furthermore, the thermoelectric physical remedy apparatus related to the present invention provides the ventilation path 11 formed inside of the belt-like external cover 12 with wind generated by blower fan 14. This effectively prevents heat from remaining inside of the belt-like external cover 12 and each thermo-module 15 from being heated. In particular, when the automatic hot-cold temperature alternating switch 7 is activated, ventilation wind effectively prevents thermal interference from occuring between hot-and-cold temperature cycles.

In addition, since the preferred embodiment of the invention employs the belt-like external cover 12 made from soft PVC material, in addition to abdomen part mentioned above, the flexible soft belt-like external cover 12 can smoothly fit against any affected part such as hands, legs, and other parts sufffering from either contusion, sprain, or muscular fatigue, and the like, thus allowing the apparatus to provide multifunctional physical treatments.

Furthermore, as described earlier, a plurality of ventilation apertures 10 are provided in vertical edges of both sides in the length direction of the belt-like external cover 12. The preferred embodiment provides a plurality of blower fans 14 and 14 inside of the apertures 10 and 10. Even when the user wears clothes above the belt-like external cover 12 of the thermoelectric physical remedy apparatus related to the invention while operating it, ventilation effect cannot be obstructed by clothes. In particular, the belt-like external cover 12 made from soft PVC material securely insulates the power-connected parts from the human body.

In addition to those objects of applying the apparatus related to the invention thus far described, the apparatus can also effectively be made available for cooling the human heat and other portions in place of a water pillow or an ice bag.

The present invention being thus described, however, it will be obvious that the same may be varied in may ways. Such variations are not regarded to be a departure from the spirit and scope of the invention, while all such modifications and variations are intended to be included within the scope of the following claims.

What is claimed is:

1. A thermoelectric physical remedy apparatus comprising
   a plurality of thermoelements for generating high and low temperatures by Peltier effect;
   a hollow elongated cover made of soft flexible material and providing a ventilation path therewithin, said plurality of thermoelements being held by said cover with part of said thermoelements being exposed outside of said cover;
   means for selectively applying electric current to said plurality of thermoelements; and
   a plurality of blower fans disposed inside of said cover and in said ventilation path therewithin.

2. The thermoelectric physical remedy apparatus defined in claim 6, wherein said means for selectively applying electric current comprises a control unit for controlling power supply to said thermoelements, wherein said control unit is provided with temperature adjusting knob, cooling-activation switch, hot-temperature generating switch, and automatic hot-cold temperature alternating switch, which are respectively workable by external operation.

3. The thermoelectric physical remedy apparatus defined in claim 1, wherein said cover comprises a belt-like configuration; and wherein a plurality of ventilation aperatures are formed at ends of said hollow cover and are connected by said ventilation path.

4. The thermoelectric physical remedy apparatus defined in claim 1, wherein said thermoelements comprise a plurality of heat radiation fins provided for each thermoelement inside of said ventilation path.

* * * * *